United States Patent [19]

Madaus et al.

[11] Patent Number: 4,511,561
[45] Date of Patent: Apr. 16, 1985

[54] LAXATIVE COMPOSITION COMPRISING PSYLLIUM SEEDS AND SENNA FRUITS

[75] Inventors: Rolf Madaus, Köln-Brück; Klaus Görler, Bensberg-Refrath, both of Fed. Rep. of Germany

[73] Assignee: Dr. Madaus & Co., Cologne, Fed. Rep. of Germany

[21] Appl. No.: 506,229

[22] Filed: Jun. 22, 1983

Related U.S. Application Data

[63] Continuation of Ser. No. 223,965, Jan. 12, 1981, abandoned, which is a continuation of Ser. No. 112,490, Jan. 16, 1980, abandoned.

[30] Foreign Application Priority Data

[DE] Fed. Rep. of Germany ...................

[51] Int. Cl.³ .............................................. A61K 35/78
[52] U.S. Cl. .................................................. 424/195.1
[58] Field of Search ........................................ 424/195

[56] References Cited

U.S. PATENT DOCUMENTS

| 1,891,697 | 7/1931 | Tavin | 424/195 |
| 1,891,698 | 7/1931 | Tavin | 424/195 |

FOREIGN PATENT DOCUMENTS

| 120M | 8/1960 | France | 424/195 |
| 856351 | 12/1960 | United Kingdom | 424/195 |
| 1135528 | 12/1968 | United Kingdom | 424/195 |

*Primary Examiner*—Albert T. Meyers
*Assistant Examiner*—John W. Rollins, Jr.
*Attorney, Agent, or Firm*—Felfe & Lynch

[57] ABSTRACT

Laxative compositions having particularly mild and well-tolerated action, not accompanied by toxic or side-effects, based on psyllium seeds and senna fruits are prepared by mixing separately ground psyllium seeds and senna fruits in a dry state, moistening the resulting ground mixture rapidly and uniformly with water, quickly granulating the resulting mixture and drying same in a manner preventing substantial swelling of the product to a residual moisture content of no more than 3.5% and then coating the composition with a pharmacologically acceptable material.

24 Claims, No Drawings

LAXATIVE COMPOSITION COMPRISING PSYLLIUM SEEDS AND SENNA FRUITS

This application is a continuation of application Ser. No. 223,965, filed Jan. 12, 1981, which is a continuation of Ser. No. 112,490, filed Jan. 16, 1980, now abandoned.

The invention relates to a laxative composition, more specifically a laxative comprising psyllium seeds and senna fruits, and to a method of preparing the same.

The use of psyllium seeds (*Plantago psyllium* L.) for preparations for the regulation of intestinal activity is known. Psyllium seed has a considerable capacity for swelling and thus stimulates physical dilation of sensitive receptors of the intestinal wall. In accordance with a known method (German Pat. No. 1,103,520), psyllium seed is finely ground, moistened with water to form a very viscous paste, and dried in strand form, then broken up and finally sugar coated.

The action of senna fruits (*Cassia angustifolia*) as a vegetable laxative is also known.

In other composite laxative medicines both psyllium seed and senna fruits are contained, and in these preparations the predominantly physical action of the psyllium seed is supported by the pharmacological stimulating action of senna fruits, to achieve a better overall effect.

The active sennosides contained in senna fruits are sensitive to oxidation and are easily oxidized to the rhein, which has a certain convulsant and pain producing action. There has thus been a need for a composition which overcomes or mitigates the possibility of undesirable side effects.

The present invention provides such a composition, i.e., a preparation in which the ground senna fruit product is protected against premature attack.

The laxative of the invention comprises ground psyllium seed (I) and senna fruits (II) and is characterized in that Component II is in a form in which it is largely enveloped by dried-on component I.

By being substantially enveloped by the psyllium component, the senna fruit component is protected against undesirable alteration and its release is furthermore retarded, so that a longer-lasting, moderated action virtually free of undesirable side effects is achieved.

This protective action may additionally be stabilized and enhanced if the mixture of the two ground components psyllium seeds ovatae and sennae fructus angutifoliae is supplemented with minor proportions of husks to make up for losses in the course of grinding of the psyllium seeds.

As compared to ground psyllium seeds the use of husks as ground product features a substantially increased swelling ability by virtue of the mucus products contained therein in a substantially higher concentration. Measures of the swelling number according to West German Pharmakopoea DAB 8, page 24, with thirty samples each resulted in an average value of 57 ml for each gram of ground psyllium seed husks whereas for the ground psyllium seeds an average value of 15 ml for each gram was found.

In accordance with the increased swelling ability of the ground psyllium seed husks, their addition increases the tendency of forming the desired enveloping of the dispersed sennae fructus particles which is particularly advantageous for a pharmaceutical application.

The weight ratio of the psyllium seed portion to the sennae fruit portion in the laxative composition according to the invention is preferably in the range of 4 to 5:1, with a weight ratio of psyllium seed portion, psyllium seed husks portion and senna fruit portion of the ground product of approximately 52:2.2:12.4 being particularly advantageous.

As now recognized psyllium seed not only contains a considerable amount of material insoluble in water, but also forms an insoluble hydrolysis residue of about 30–35%. This, together with a neutralizing action of certain components of psyllium seed, seems to be the reason for the favorable characteristics of the new compositions comprising comminuted senna fruits prevailingly enveloped by a protective psyllium seed coating.

To make such preparations, separately ground psyllium seeds and senna fruits are mixed together dry, and the mixture, rapidly and uniformly moistened with about 50% water, is so quickly granulated and dried that substantial swelling of the product is suppressed, and the granules, dried to a residual moisture content of no more than 3.5%, are then sugar coated.

According to a preferred embodiment the ground psyllium seeds and senna fruits are kneaded with 30 to 40% by weight of water adding approximately 3 to 4% by weight of ground psyllium seed husks, whereby only a limited swelling occurs. In this swollen state the mucic products of the ground psyllium ovatae husks have a sufficient ability for spreading in view of a sufficient immobilisation of the water in the swollen layers, with an appropriate ability for further processing of the mass being maintained nevertheless. Greater amounts of water, however, cause processing problems, while the lyospheres are at sublimit values upon addition of insufficient amounts of water so that the spreading may not be achieved as desired.

Prior to the grinding the psyllium seeds and senna fruits are conveniently dried to a moisture content of 3.5% at a temperature of 80° C. and the sennoside content of the senna fruit component is adjusted at 2.0 to 2.5% by weight, preferably at approximately 2.2% by weight by combining different lots. During the grinding operation the temperature of the ground material should not exceed 80° C.

In the moistening of the dry mixed ground products of psyllium seed and senna fruits with water, provision must be made to prevent substantial swelling of the ground psyllium component (represented by a swelling number of about 16), by rapid and uniform moistening and thorough mixing. The fines contained in the ground product of psyllium seeds, however, swell so rapidly that the vehicle (water) becomes a mucilage resulting in an enveloping of the sensitive senna fruit component.

It has been found that when proceeding in accordance with the process of the invention, there occurs a favorable and beneficial pH adjustment, the effect of which is that an initially acid pH (e.g., pH 5.5–6.0) is shifted toward the neutral point, i.e., pH 7.0, by action of the components being mixed; the mixture thus exhibits a desirable characteristic, apparently by undergoing a reaction or reactions which produce alkaline components. This effect is important because sennoside products are generally sensitive to acid or alkali media, which lead to instability and undesired oxidation; since the process of the invention leads to an inherently pH neutral product, the stability thereof is desirably enhanced.

In order to achieve a rapid and uniform moistening of the mixture of ground products, each time only small amounts of grinding product mixture, as well as water, should be combined successively (especially in a continuous matter) and subjected to intensive mixing in a series of mixing operations. Preferably this is accomplished in a plurality of sequential screw blenders.

In this manner, a uniform paste is produced within a few minutes and the material is delivered to the granulator which must also be a fast-operating machine. Preferably, therefore, an extrusion press having a large D ratio, at whose output a separately drive, revolving chopper provides for immediate chopping of the emerging strand into granules of sizes ranging around 2 to 2.5 mm, is used.

The granulated material is preferably dried in a fluidized bed using air, in which a rapid, gentle drying is achieved, and caking of material is prevented. We found that the granulated material, of which only the fines are swollen with moisture, undergoes this process without appreciable shrinkage and can be delivered in the resultant form to the fina, sugar-coated operation.

Preferably, psyllium husks (especially in an amount compensating for psyllium husk portions possibly lost during the comminution of the psyllium seed) and tragacanth gum are added in small amounts to the mixture to be granulated; this increases the swelling component of the laxative and produces an additional binding action.

The weight ratios of admixture of the ground psyllium seeds and senna fruits range especially from about 4:1 to 5:1, a controlled sennoside content of about 2.5% being maintained in senna fruit component by combining different lots. Psyllium husks and tragacanth gum are added, preferably in amounts of 3 to 4% by weight (husks) and 1 to 1.5% (tragacanth gum), based on the combined mixture of ground psyllium seeds and senna fruits.

Psyllium seeds and senna fruits are ground separately to approximately the same grain size distribution, preferably to approximately the following sieve analysis:
99% finer than 500 μm,
85% finer than 400 μm,
50% finer than 200 μm.

An especially preferred laxative contains especially about 75% psyllium seed, approximately 20% senna fruits, approximately 3.2% additional psyllium husks, and about 0.8% gum tragacanth.

A particularly preferred embodiment of the above described product consists essentially of the following:
psyllium seeds ovatae: 52.000 parts by weight
psyllium seeds ovatae (husks): 2.200
sennae fructus angustifoliae: 12.400
talcum: 12.459
gum arabic: 1.400
ferrum oxydatum E 172: 0.697
Color Index (1956): 77 452, 77 499, 77 491
gum tragacanth: 0.750
oleum carvi: 0.035
oleum slaviae: 0.035
oleum menthae piperitae: 0.070
paraffinum subliquidum: 0.240
paraffinum durum: 0.111
saccharum: 17.604
per 100 parts by weight of composition.

A further particularly preferred embodiment comprises the following components:
psyllium seeds ovataei: 54.200 parts by weight
sennae fructus angustifoliae: 12.400
usual additives, as described above.

During the overall preparation a control of the bacteria number should be continuously maintained.

The mode of preparation and the type and amount of the constituents of the laxative provide advantageous properties as compared to known laxatives of this type. These advantages consist in that by the physiologically appropriate swelling of the product the bowel is provided with a filling which is necessary for an optimum natural bowel activity. Further, undesired side effects are eliminated, for example an irritation of the mucuous membranes of the stomach and the bowel and a careful and attenuated release of the intact sennosides is ensured. These pharmacologically and clinically observed particular advantages will become better understood by way of model tests on the kinetics of the sennoside release:

To evidence the protecting enveloping action of the dried-on mucic products of psyllium seed (husks) ground products, extraction tests were performed in water of a temperature of 23° C. and in artificial gastric juices and artificial bowel juices (each at a temperature of 37° C.) using 12.4 g of ground sennae fructus angustifoliae (I), a mixture of 12.4 g of ground sennae fruit and 54.2 g ground psyllium seeds (II) and the laxative according to the invention comprising 12.4 g sennae fruit ground products and 54.2 g psyllium seeds ground products (III).

The above ground products were stirred in 300 ml extraction liquid each for 10 and 30 minutes, respectively. The liquid was separated from the insolubles by centrifuging and lyophilized. After determining the weight each, the content of sennosides was determined according to the modified procedure of the European Pharmakopoea EuAb 2 and put into a relationship with the amount of sennosides contained in the lots used for each experiment. The following table shows the data obtained in these tests.

| Tested material | Percentage of extracted Sennosides | | | | | |
|---|---|---|---|---|---|---|
| | Water | | artificial gastric juices | | artificial bowel juices | |
| | 10 min | 30 min | 10 min | 30 min | 10 min | 30 min |
| I | 85.2% | 88.9% | 55.6% | 59.3% | 74.1% | 74.1% |
| II | 55.6% | 59.3% | 40.7% | 44.4% | 48.2% | 59.3% |
| III | 13.0% | 8.9% | 6.7% | 2.2% | 3.2% | 5.6% |

These data clearly show a retarded release of the sennosides for the laxative composition according to the invention.

The retarded release of the sennosides from the laxative composition according to the invention does not result in a complete blocking of the active ingredients, which, to the contrary are substantially completely released over longer periods of time as evidenced by the following in vitro test:

The laxative composition of the invention was allowed to swell overnight. Thereafter the swollen material was additioned with water and extracted five times with the water phase being renewed after each hour. After five hours extraction approximately 84% of the expected sennosides could be isolated from the aqueous phases. The individual data are listed in the following table.

| Determination of the Sennoside Release Rate from Swollen Laxative Composition | | | |
| --- | --- | --- | --- |
| Extraction | Solids (g) | Sennosides (g) | dissolved Sennoside portion (%) |
| 1. | 20.73 | 0.126 | 46.67 |
| 2. | 6.56 | 0.051 | 18.89 |
| 3. | 2.98 | 0.026 | 9.63 |
| 4. | 1.53 | 0.014 | 5.18 |
| 5. | 1.15 | 0.009 | 3.33 |
| Total | | 0.226 | 83.7 |

Upon using artificial gastric juices and artificial bowel juices, respectively, essentially the same data are obtained.

The above tests, which are approximated to the mean duration of residence of the drugs in the gastro-intestinal tract clearly show that essentially all of the Sennosides of the sennae fruit component in the laxative composition according to the invention will be effective with the desired retardation.

The above results and further results as described in the examples which follow, show that the laxative composition has a smooth action free of undesired side effects and is characterized by a particularly high tolerability, particularly as an aid to defacation for haemorrhoid or fissure patients before and after surgery. They may be administered in a clinical application to patients confined to bed over prolonged periods of time and may be administered also during pregnancy without concern.

PREPARATION EXAMPLE

Psyllium seeds were cleaned of dirt and foreign seeds, dried at about 80° C. to a moisture content of 3.5%, and ground to a grain size distribution corresponding to the following sieve analysis 99% finer than 500 μm
85% finer than 400 μm
50% finer than 200 μm.

In the grinding process the material must not be heated above 80° C.

Senna follicles were tested separately for their sennoside content and standardized at 2.2% by the mixing of different lots, if necessary. The grinding of this material to a size corresponding to the size specified above for psyllium seeds was performed in two stages, namely a preliminary grinding and a fine grinding.

The two ground products were mixed dry with 4.4 kg of ground psyllium husks and 1.5 kg of tragacanth gum in the following ratio:

| | |
| --- | --- |
| psyllium seeds: | 105.500 kg |
| senna fruits: | 27.600 kg |
| husks and gum: | 5.900 kg |
| | 138.000 kg |

This pre-granulate resulted, after the below-described granulation and dragee formation procedure, in 200 kg of final laxative product.

The powder mixture passed from the mixing vessel to the mixing section feeding the strand extruder, in which approximately 30-40% of filtered water was added. This moist mass was allowed to stand for 1-2 hours in order to promote spreading of the mucilage around the senna fruit particles. The material was then rapidly mixed and fed to the extruder where it was extruded with a large D-ratio at a pressure of about 50 atmospheres excess pressure and chopped by a rotating knife at the die into granules from 2.1 to 2.2 mm long. The moist granular product is to have a moisture content of 35%.

The drying operation that follows was performed in a fluidized bed dryer with vibratory feed, to a residual moisture content of no more than 3.5% within about 25 minutes at an air temperature of 125° C. and an air flow rate of 8000 cubic meters per hour.

The dry granules were sifted to remove those smaller than 1 mm and those over 3 mm, and then their bulk weight was from 510 to 530 grams per liter. Finally the material was formulated into dragees by contacting the above "pre-granulate" with a dragee suspension comprising aromatic essences, gum arabic, saccharose pigment and talcum which was applied to the pre-granulate in a conventional dragge-making machine. This resulted in a sugar-coated dragge incorporating therein a flavoring mixture of peppermint oil, caraway oil and sage oil (ratio 2:1:1) in amounts of approx. 0.1% with respect to the final product. The bacteria count of the material was constantly inspected during the entire process.

The final product, which is the particularly preferred embodiment of the invention because of its outstanding pharmacological properties, had the following composition (per 100 kilograms of product):

Psyllium seeds ovatae: 52.000 kg
Supplementary Psyllium husks: 2.200 kg
Sennae fructus angustifoliae: 12.400 kg
Talcum: 12.459 kg
Gum arabic: 1.400 kg
Ferrum oxydatum, E 172: 0.697 kg
Color Index (1956): 77492, 77499, 77491,
Gum tragacanth: 0.750 kg
Oleum carvi: 0.035 kg
Oleum salviae: 0.035 kg
Oleum menthae piperitae: 0.070 kg
Paraffinum subliquidum: 0.240 kg
Paraffinum durum: 0.110 kg
Saccharum: 17.604 kg The above product has a swelling number of about 7.50 (at leat 6.0) (determined according to West German Pharmakopoea DAB 8), a bulk density of 0.765 to 0.905 g/ml (determined according to DIN 53 912), a granula diameter of 1 to 3 mm and a sennoside content of 0.25% to 0.31% particularly of 0.27%. These parameters ensure a particularly good overall action.

A further preferred embodiment consists of the following:

Psyllium seeds ovatae, ground product: 54.200 kg
Sennae fructus angustifoliae: 2.200 kg
Usual additives as above.

The parameters of this further preferred embodiment are in the same range.

The laxatives of the invention are characterized by their mild, reliable action combined with complete tolerability. The compositions of the invention are also characterized by stable effectiveness over long periods, no habituation phenomena having been observed.

To establish the pharmacological safety of the laxatives of the invention, the embodiment set forth in the above preparation example was tested as follows:

Toxicity and Side Effect Tests

Acute toxicity was tested in rats and mice of both sexes, using 40 of each. The powdered material was suspended in water and the fresh suspension administered per os to the animals, which were observed for eight days. The precise determination of the $LD_{50}$ proved to be impossible because the toxicity was too low. Even one hundred times the daily dose recommended for human beings produced no harmful effect.

$LD_{50}$ (Per os):
in the rat: 5 g/kg;
in the mouse: 10 g/kg.

In additional tests for the subacute toxicity in rats and mice, no mortality was observed in the administration per os of 0.5, 1.0 and 2.0 g/kg over a period of 15 days. To test for the chronic toxicity, a dose of 0.5 g/kg and 1.0 g/kg was administered per os to two groups of rats (Sprague-Dawley) of 150 g body weight, of male and female sex.

Tests were made for weight gain, erythrocyte count, leucocyte count, differential white count, blood sugar, prothrombin time, transaminases and residual nitrogen before and after treatment. No marked changes were observed in comparison with a control group of animals.

After the tests were completed, all of the animals were killed and subjected to a complete autopsy. The weight of the spleen, liver, heart, kidneys, brain, suprarenal gland, thyroid gland, testes and hypophysis showed no marked anomalies in comparison with the control animals. Histologically, virtually no changes were observed with regard to cellular infiltration, fatty infiltration and adenomatose hyperplasia of the liver, nephrosis, sinusoidal dilatation of the adrenals, cellular infiltration of the heart, adenomatose hyperplasia of the thyroid, and infiltration of the cells of the spleen and testes.

In another series of toxicity tests the subacute toxicity of the composition of the invention, administered over thirty days, was investigated both in rats and dogs and in still another series of safety tests chronic toxicity was determined both in rats and dogs by administration over a period of 180 days. Oral administration of the inventive composition for thirty consecutive days in doses five and ten times higher than those recommended for human consumption was well tolerated by rats and dogs of both sexes. Oral administration of the composition over a period of 180 days in doses tow-and-a-half and five times higher than those recommended for human consumption was well tolerated by Sprague-Dawley rats and mongrel dogs of both sexes. During and after the treatment there were no changes observed in the following parameters: development of body weight, hematological, blood chemistry, and unrinological parameters, macroscopic and microscopic examination of the principal organs. In particular there was no incidence of bleeding or ulceration of the gastrointestinal tract.

Studies on the rabbit, with a daily administration of 1.0 g/kg for 6 weeks to male and female animals by administration per os, gave no indication of any harmful effects as regards body weight, erythrocyte count, leucocyte count, differential white count, residual nitrogen and blood sugar.

The teratogenic action of the product was tested in rats and rabbits with daily doses of 1 g/kg per os, which were administered from the 7th to 21st day of pregnancy in the rat and from the 7th to the 15th day in the rabbit. The fetuses were removed from the animals on the 21st and 27th day, respectively, and examined. No specific teratogenetic effect of the product was found, and evidently the inventive composition has no effect on embryonic development.

Laxative Action Tests

For the testing of the laxative action itself, single doses of 2.5 and 5 g/kg were administered per os respectively to mice and rats. A decided increase and softening of the feces was observed. A definitely dose-related effect is observed 3 to 4 hours after administration. The influence of the product on intestinal motility and on the time required for the passage of the intestinal contents was tested in rats (strain Sprague-Dawley) of both sexes weighing 240 g, in groups of 10 animals each. After 24 days of fasting, the animals were administered per os 22 ml/kg of aqueous suspension of 10% animal charcoal and 0.5% carboxy-methylcellulose, as well as 2.5 and 5 g/kg, respectively, of the product under test. Forty minutes after administration the animals were killed and the total length of the small intestine and the suspension-filled length of same were measured. The following results were obtained:

| Treatment | Dose g/kg | Intestinal fill length (cm) |
|---|---|---|
| — | — | 56 ± 4.4 |
| Laxative | 2.5 | 79 ± 6.2 |
| Laxative | 5 | 86 ± 6.8 |

In another series of tests the laxative action of the inventive composition was determined by administration of the test substance at different dosage levels to mice and rats.

The test procedure was as follows:

An equal number of male and female mice (strain Swiss) with a mean body weight of 24 g and the same number of male and female rats (strain Sprague-Dawley) with a mean body weight of 230 g were used. After withdrawing food from the animals for 3 hours, they were housed in a compartmentalized cage. The floor of the cage was covered with filter paper in order to collect the fecal pellets of each animal. The animals which excreted soft fecal pellets were rejected from the experiment.

The remaining animals were placed in the treatment cage. The test composition was administered p.o. using an oral syringe at 2.5 and 5 g/kg. At regular time intervals, up to 8 hours after the administration of the inventive composition, the number and nature of the fecal pellets excreted by each animal was observed. The results are set forth in the tables below (wherein the "Test Comp" is the inventive composition):

| Investigation of the laxitive effect in the rat. (single dose of 2.5 and 5.0 g/kg p.o.) | | | | | | | | | |
|---|---|---|---|---|---|---|---|---|---|
| | | | Observation period (no. of hours after administration) | | | | | | |
| | | | 2 | | 4 | | 6 | | 8 |
| n | Treatment | g/kg | H | S | H | S | H | S | H | S |
| 10 | controls | — | 2.4 | 0.1 | 3.8 | 0.1 | 4.5 | 0.1 | 4.5 | 0.1 |
| 10 | Test Comp | 2.5 | 3.1 | 0.2 | 3.8 | 2.2 | 4.2 | 6.2 | 5.4 | 6.8 |

-continued

| n | Treatment | g/kg | | | | | | | |
|---|---|---|---|---|---|---|---|---|---|
| 10 | Test Comp | 5 | 3.3 | 4.1 | 3.9 | 6.1 | 4.4 | 7.2 | 4.9 | 9.1 |

H = hard faeces: No. of faecal pellets per rat
S = soft faeces: No. of faecal pellets per rat Investigation of the laxative effect in the mouse.
(single dose of 2.5 and 5.0 g/kg p.o.)

| | | | Observation period (no. of hours after administration) | | | | | | | |
|---|---|---|---|---|---|---|---|---|---|---|
| | | | 2 | | 4 | | 6 | | 8 | |
| n | Treatment | g/kg | H | S | H | S | H | S | H | S |
| 20 | controls | — | 3.1 | 0.1 | 4.2 | 0.1 | 4.4 | 0.2 | 4.5 | 0.2 |
| 20 | Test Comp | 2.5 | 2.4 | 0.2 | 4.2 | 2.1 | 5.1 | 3.3 | 5.3 | 3.8 |
| 20 | Test Comp | 5 | 2.6 | 3.4 | 4.4 | 5.6 | 4.6 | 8.2 | 4.6 | 9.8 |

H = hard faeces: No. of faecal pellets per mouse
S = soft faeces: No. of faecal pellets per mouse Investigation of the laxative effect in the rat.
(single dose of 2.5 and 5.0 g/kg p.o.)

| | | | No. of rats with soft faeces/ No. of treated animals Hours after administration | | | |
|---|---|---|---|---|---|---|
| n | Treatment | g/kg | 2 | 4 | 6 | 8 |
| 10 | controls | — | 0/10 | 0/10 | 2/10 | 2/10 |
| 10 | Test Comp | 2.5 | 3/10 | 5/10 | 5/10 | 6/10 |
| 10 | Test Comp | 5 | 3/10 | 7/10 | 10/10 | 10/10 |

With these animals obviously at a dosis above 2.5 g/kg the upper limit with regard to an increase of activity is reached.

Investigation of the laxative effect in the rat.
(single dose of 2.5 and 5.0 g/kg p.o.)

| | | | No. of mice with soft faeces/ No. of treated animals Hours after administration | | | |
|---|---|---|---|---|---|---|
| n | Treatment | g/kg | 2 | 4 | 6 | 8 |
| 20 | controls | — | 0/20 | 1/20 | 4/20 | 4/20 |
| 20 | Test Comp | 2.5 | 4/20 | 8/20 | 10/20 | 17/20 |
| 20 | Test Comp | 5 | 8/20 | 17/20 | 20/20 | 20/20 |

The results showed a distinct laxative action demonstrated by the increased frequency of defecation and also by a substantial increase in soft fecal pellets in comparison with hard fecal pellets.

In a test for diuresis, a reduction of kidney secretion was observed, which appears to be connected with the increase in the enteral fluid excretion. In a test for choleretic action, virtually no significant change was detected, and from this it is concluded that the product of the invention has no choleretic action. The daily food intake was also tested; virtually no change was found.

The product administered per os in doses of 1.0 and 2.0 g/kg to male rats to 280 grams weight produced no perceptible changes in arterial blood pressure and heart rate. Also, no inflammatory changes in the gastrointestinal area were detected.

In summary, the test results established that the inventive composition has very low toxicity, i.e., even too low to determine the $LD_{50}$ in the in vivo experiments in which the inventive composition was administered in dosages 100 times those recommended for human therapy. No toxic effects or intolerance were observed, only laxative action, i.e., its main pharmocological property. In addition, no inflammatory changes in the gastric and intestinal regions of animals receiving one large dose of the composition or long-term treatment therewith was established and this is regarded as surprising since inflammatory changes are frequently observed in animals treated with laxatives. In gravid animals the administration of the inventive composition did not evoke any changes in normal fetal development and the test animals were totally comparable to those of control animals with regard to number, weight and appearance of the fetuses.

The laxative action of the invention composition was found to occur between 3 and 4 hours after administration to the animals and was directly dosage related. The laxative action is accompanied by an acceleration of the transit time of contents through the intestine. The diuresis experiments with treated animals resulted in a diminution of urine output which can be related to the increase in enteral fluid excretion. No changes in bile secretion, smooth muscle function, arterial blood pressure or heart rate were demonstrated. Daily food intake was also not affected by the administration of the inventive composition.

The laxatives of the invention are generally applied at daily dosages of approximately 1 to 5 grams per 75 kg of body weight to patients suffering from constipation and for the regulation of the stool. The laxatives can be formulated in a conventional manner with the addition of flavoring substances and the like. The addition of peppermit oil, caraway oil and sage oil to sugar-coated preparations have proven to be desirable in giving pleasantly administered dragees.

When percentages are referred to hereinabove, percentage by weight is intended, unless otherwise stated.

It will be understood that the specification and examples are illustrative but not limitative of the present invention and that other embodiments within the spirit and scope of the invention will suggest themselves to those skilled in the art.

What is claimed is:

1. In a method of preparing a laxative based on pysllium seeds and senna fruits, the improvement comprising:
   a. separately grinding the psyllium seeds and senna fruits;
   b. mixing the separately ground pysllium seeds and senna fruits in a dry state into a dry mixture;
   c. further mixing and rapidly and uniformly moistening the dry mixture with sufficient water to prevent substantial swelling of the ground pysllium seeds therein while allowing sufficient swelling thereof to form a mucilage which, from the further mixing, envelops the ground senna fruits, whereby to reduce the undesirable alteration of the senna fruit component and to retard release thereof; and
   d. quickly granulating and drying the further mixed and moistened product to a product having residual moisture content of about 3.5% by weight of water in a manner preventing further substantial swelling of the pysllium therein, whereby a laxative is obtained having longer lasting moderated action and substantially lessened undesirable side effects including convulsant and pain producing actions, upon use of the said laxative.

2. Method as claimed in claim 1, and further comprising: adding ground pysllium seed husks to the mixture to be granulated, whereby the enveloping of said ground senna fruit by. psyllium is enhanced and the resultant product exhibits substantially increased swelling ability.

3. Method of claim 1 wherein psyllium seed husks and tragacanth gum are added to the mixture to be granulated.

4. Method as claimed in claim 3 wherein the amount of said supplementary husks is about 3 to 4% and the amount of tragacanth gum is about 1 to 1.5%, based on the total amount of ground psyllium seeds and senna fruits.

5. Method of claim 1 comprising the additional step of pressing the granulated and dried product of step (d) into a unit which is coated with a pharmacologically acceptable material whereby to further reduce the side effects of the ground senna fruits.

6. Method of claim 5 wherein said pharmacologically acceptable material comprises aromatic essences, gum arabic, saccharose pigment and talcum.

7. Method of claim 1 wherein said moistening of the dry mixture is accomplished by addition of about 50% water by weight, based on the moistened total mixture.

8. Method of claim 1 wherein the amount of said water is about 30 to 50 percent by weight, based on the moistened total mixture.

9. Method as claimed in claim 1 wherein said moistening is performed by continuously combining relatively small amounts of each grinding product mixture and water in a plurality of successive mixing stages.

10. Method as claimed in claim 9 wherein said mixing is carried out in a plurality of screw mixers.

11. Method as claimed in claim 1 wherein said granulating step is performed in an extrusion press fitted with a separately controllable chopping knife at the press outlet.

12. Method as claimed in claim 1 wherein said granulating step is performed at approximately 50 atmospheres of excess pressure and to result in particle sizes in the range of approximately 2 to 2.5 mm.

13. Method as claimed in claim 1 wherein said granules are dried in air in a fluidized bed for approximately half an hour.

14. Method as claimed in claim 1 wherein psyllium seeds and senna fruits are initially ground separately to a grain size distribution of approximately
    99% finer than 500 um
    85% finer than 400 um
    50% finer than 200 um.

15. Method as claimed in claim 1 wherein the ground psyllium seeds and senna fruits are mixed in a mixture ratio of about 4:1 to 5:1 (psyllium:senna).

16. Method as claimed in claim 1 comprising an additional step of adjusting the sennoside content of the senna fruits prior to grinding thereof to a standard value in the range of 2.0 to 2.5% by weight.

17. Method as claimed in claim 16 wherein the sennoside content of the senna fruits is adjusted to a standard value of 2.2% by weight.

18. Laxative composition produced by the method of claim 1.

19. Laxative composition of claim 18 comprising approximately:
    52% by weight psyllium seeds
    13% by weight senna fruits
    2% by weight supplementary psyllium husks
    0.8% by weight tragacanth gum.

20. Laxative composition of claim 18 consisting essentially of the following:
    Psyllium seeds ovatae: 52.000 parts by weight
    Supplementary psyllium husks: 2.200 parts by weight
    Sennae Fructus Angustifoliae: 12.400 parts by weight
    Talcum: 12.459 parts by weight
    Gum arabic: 1.400 parts by weight
    Ferrum oxydatum, E 172: 0.697 parts by weight
    Gum tragacanth: 0.750 parts by weight
    Oleum carvi: 0.035 parts by weight
    Oleum salviae: 0.035 parts by weight
    Oleum menthae piperitae: 0.070 parts by weight
    Paraffinum subliquidum: 0.240 parts by weight
    Paraffinum durum: 0.110 parts by weight
    Saccharum: 17.604 parts by weight
per 100 parts by weight of composition.

21. Laxative composition of claim 18 consisting essentially of the following:
    Psyllium seeds ovatae: 54.200 parts by weight
    Sennae Fructus Angustifoliae: 12.400 parts by weight
    Talcum: 12.459 parts by weight
    Gum arabic: 1.400 parts by weight
    Ferrum oxydatum, E 172: 0.697 parts by weight
    Gum tragacanth: 0.750 parts by weight
    Oleum carvi: 0.035 parts by weight
    Oleum salviae: 0.035 parts by weight
    Oleum menthae piperitae: 0.070 parts by weight
    Paraffinum subliquidum: 0.240 parts by weight
    Paraffinum durum: 0.110 parts by weight
    Saccharum: 17.604 parts by weight
per 100 parts by weight of composition.

22. Laxative composition produced by the method of claim 2.

23. Laxative composition produced by the method of claim 3.

24. Laxative composition produced by the method of claim 5.

* * * * *